(12) United States Patent
Nakamura

(10) Patent No.: US 11,291,368 B2
(45) Date of Patent: Apr. 5, 2022

(54) OPHTHALMOLOGIC APPARATUS AND METHOD OF CONTROLLING THE SAME

(71) Applicant: TOPCON CORPORATION, Tokyo (JP)

(72) Inventor: Shunsuke Nakamura, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 65 days.

(21) Appl. No.: 16/297,760

(22) Filed: Mar. 11, 2019

(65) Prior Publication Data

US 2019/0282092 A1 Sep. 19, 2019

(30) Foreign Application Priority Data

Mar. 16, 2018 (JP) .............................. JP2018-049844

(51) Int. Cl.
*A61B 3/15* (2006.01)
*A61B 3/00* (2006.01)
*A61B 3/135* (2006.01)

(52) U.S. Cl.
CPC .............. *A61B 3/15* (2013.01); *A61B 3/0058* (2013.01); *A61B 3/0083* (2013.01); *A61B 3/135* (2013.01); *A61B 3/0025* (2013.01)

(58) Field of Classification Search
CPC ......... A61B 3/15; A61B 3/0025; A61B 3/135; A61B 3/0083; A61B 3/0058; A61B 3/152;
(Continued)

(56) References Cited

U.S. PATENT DOCUMENTS

2006/0268230 A1 11/2006 Kogawa et al.
2007/0146636 A1 6/2007 Ishikura
(Continued)

FOREIGN PATENT DOCUMENTS

CN 1989894 A 7/2007
CN 102670173 A 9/2012
(Continued)

OTHER PUBLICATIONS

Office Action dated Aug. 5, 2019 issued in corresponding Great Britain Patent Application No. 1903038.6, 7 pages.
(Continued)

*Primary Examiner* — Stephone B Allen
*Assistant Examiner* — Gabriel A Sanz
(74) *Attorney, Agent, or Firm* — Xsensus LLP

(57) ABSTRACT

An ophthalmologic apparatus includes a data acquisition unit, a movement mechanism, an image acquisition unit, an analyzer, and a controller. The data acquisition unit is configured to optically acquire data of a fundus of a subject's eye. The movement mechanism is configured to change relative position between the subject's eye and the data acquisition unit. The image acquisition unit is configured to acquire an image of the fundus. The analyzer is configured to specify at least one of a relative movement direction and
(Continued)

relative movement amount of the data acquisition unit with respect to the subject's eye based on a flare region in the image and a reference position in the image. The controller is configured to control the movement mechanism based on the at least one of the relative movement direction and the relative movement amount.

17 Claims, 9 Drawing Sheets

(58) Field of Classification Search
CPC ......... A61B 3/1225; A61B 3/14; A61B 3/102; A61B 3/0008; A61B 3/0016; A61B 3/12
See application file for complete search history.

(56) References Cited

U.S. PATENT DOCUMENTS

| | | | |
|---|---|---|---|
| 2012/0218518 A1 | 8/2012 | Wada | |
| 2012/0242955 A1 | 9/2012 | Yoshino et al. | |
| 2012/0249952 A1 | 10/2012 | Sakagawa | |
| 2012/0249961 A1 | 10/2012 | Muto | |
| 2014/0028976 A1* | 1/2014 | Tanassi | A61B 3/12 351/208 |
| 2015/0085252 A1* | 3/2015 | Fujimura | A61B 3/0058 351/208 |
| 2016/0100754 A1 | 4/2016 | Dobashi | |
| 2016/0345822 A1 | 12/2016 | Fujimura et al. | |
| 2019/0059723 A1 | 2/2019 | Ono | |

FOREIGN PATENT DOCUMENTS

| | | |
|---|---|---|
| CN | 102727174 A | 10/2012 |
| CN | 102727177 A | 10/2012 |
| CN | 103976708 A | 8/2014 |
| CN | 105662332 A | 6/2016 |
| CN | 107184178 A | 9/2017 |
| EP | 1736097 A1 | 5/2006 |
| EP | 2689719 A1 | 7/2013 |
| EP | 3449807 A1 | 8/2018 |
| JP | 2006-325936 A | 12/2006 |
| JP | 2012-196324 A | 10/2012 |
| JP | 2013-244363 A | 12/2013 |
| JP | 2013-248376 A | 12/2013 |
| JP | 2014-023768 A | 2/2014 |
| JP | 2016-077337 A | 5/2016 |

OTHER PUBLICATIONS

Office Action dated Apr. 28, 2021, in corresponding Chinese patent Application No. 201910199359.9, 21 pages.
Office Action dated Dec. 21, 2021, in corresponding Japanese patent Application No. 2018-049844, 8 pages.

* cited by examiner

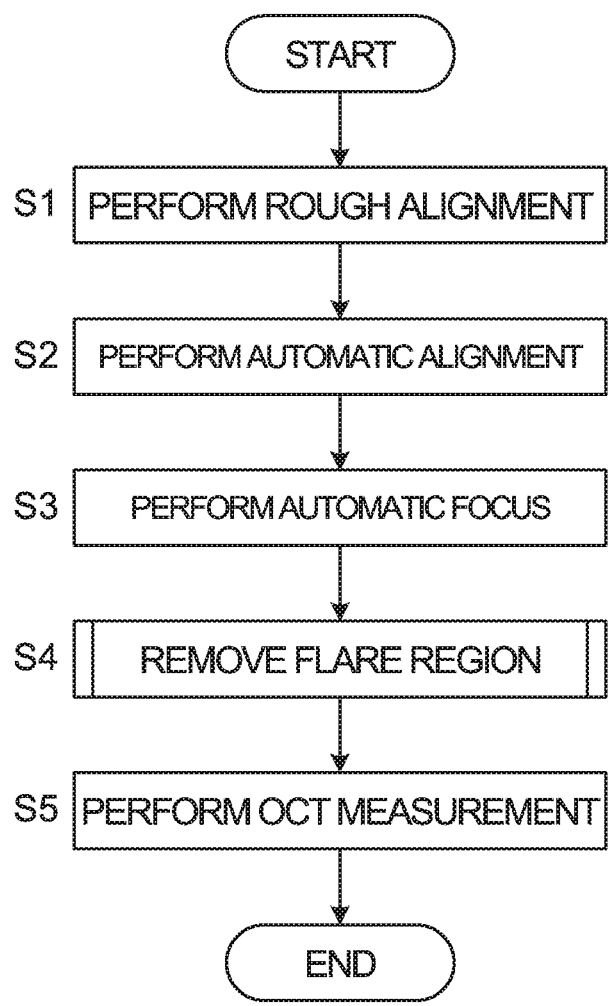

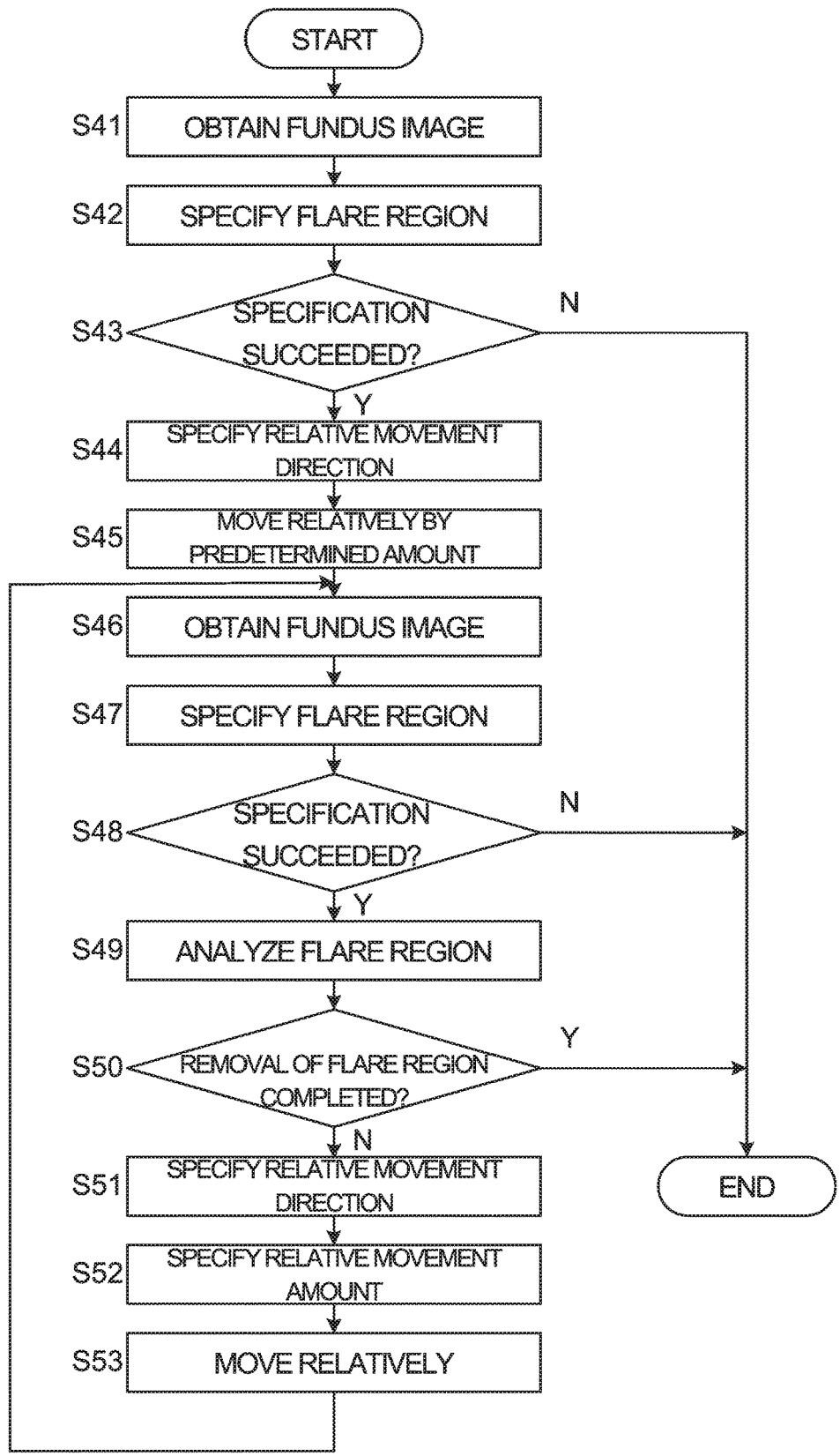

OPHTHALMOLOGIC APPARATUS AND METHOD OF CONTROLLING THE SAME

CROSS-REFERENCE TO RELATED APPLICATION

This application is based upon and claims the benefit of priority from Japanese Patent Application No. 2018-049844, filed Mar. 16, 2018; the entire contents of which are incorporated herein by reference.

FIELD

Embodiments according to present invention described herein relate to an ophthalmologic apparatus and a method of controlling the same.

BACKGROUND

Types of ophthalmologic apparatuses include ophthalmologic imaging apparatuses for obtaining images of a subject's eye, ophthalmologic measuring apparatuses for measuring characteristics of a subject's eye, and ophthalmologic therapy apparatuses for treating a subject's eye.

Examples of the ophthalmologic imaging apparatuses include an optical coherence tomography (OCT) apparatus for capturing tomographic images using OCT, a fundus camera for photographing the fundus, a scanning laser ophthalmoscope (SLO) for capturing images of the fundus by laser scanning with the use of a confocal optical system, slit lamp microscopes, operating microscopes, and the like.

Examples of the ophthalmologic measuring apparatuses include eye refraction test apparatuses (refractometer, keratometer) for measuring the refractive properties of the subject's eye, tonometers, specular microscopes for obtaining the properties of the cornea (corneal thickness, cell distribution, etc.), wave-front analyzers for obtaining the aberration information of the subject's eye using a Hartmann-Shack sensor, perimeters for measuring states of visual field, mircoperimeters, and the like.

Examples of the ophthalmologic therapy apparatuses include laser therapy apparatuses for projecting laser light onto the site to be treated such as diseased are, surgical apparatuses for specific purpose (cataract surgery, keratorefractive surgery etc.), surgical microscopes, and the like.

In many ophthalmologic apparatuses, the inspection optical system is focused on the site such as the fundus to perform imaging or the like, after the alignment between the subject's eye and the inspection optical system is completed. It is known that flare caused by the state of the subject's eye or the like appears in the image obtained by this imaging and the image may be deteriorated in some cases. For example, such deterioration of the image is caused in the case that the subject's eye is directed obliquely due to the heterophoria or the like, the case that the cornea is distorted due to the disease of the cornea or the like, the case that the subject's eye is a small pupil, and the like. Therefore, some ophthalmologic apparatuses for preventing deterioration of images due to such flare have been proposed (for example, see Japanese Unexamined Patent Application Publication No. 2006-325936, Japanese Unexamined Patent Application Publication No. 2012-196324, and Japanese Unexamined Patent Application Publication No. 2014-023768).

SUMMARY

One aspect of some embodiments is an ophthalmologic apparatus including a data acquisition unit configured to optically acquire data of a fundus of a subject's eye; a movement mechanism configured to change relative position between the subject's eye and the data acquisition unit; an image acquisition unit configured to acquire an image of the fundus; an analyzer configured to specify at least one of a relative movement direction and relative movement amount of the data acquisition unit with respect to the subject's eye based on a flare region in the image and a reference position in the image; and a controller configured to control the movement mechanism based on the at least one of the relative movement direction and the relative movement amount.

Another aspect of some embodiments is a method of controlling an ophthalmologic apparatus including a data acquisition unit configured to optically acquire data of a fundus of a subject's eye, a movement mechanism configured to change relative position between the subject's eye and the data acquisition unit, and a controller configured to control the movement mechanism, the method comprising: an acquisition step of acquiring an image of the fundus; an analyzing step of specifying at least one of a relative movement direction and relative movement amount of the data acquisition unit with respect to the subject's eye based on a flare region in the image and a reference position in the image; and a control step of controlling the movement mechanism based on the at least one of the relative movement direction and the relative movement amount.

BRIEF DESCRIPTION OF THE DRAWINGS

FIG. 7 is a schematic diagram illustrating an example of an operation of the ophthalmologic apparatus according to the embodiments.

FIG. 8 is a schematic diagram illustrating an example of an operation of the ophthalmologic apparatus according to the embodiments.

DETAILED DESCRIPTION

Figure 1:
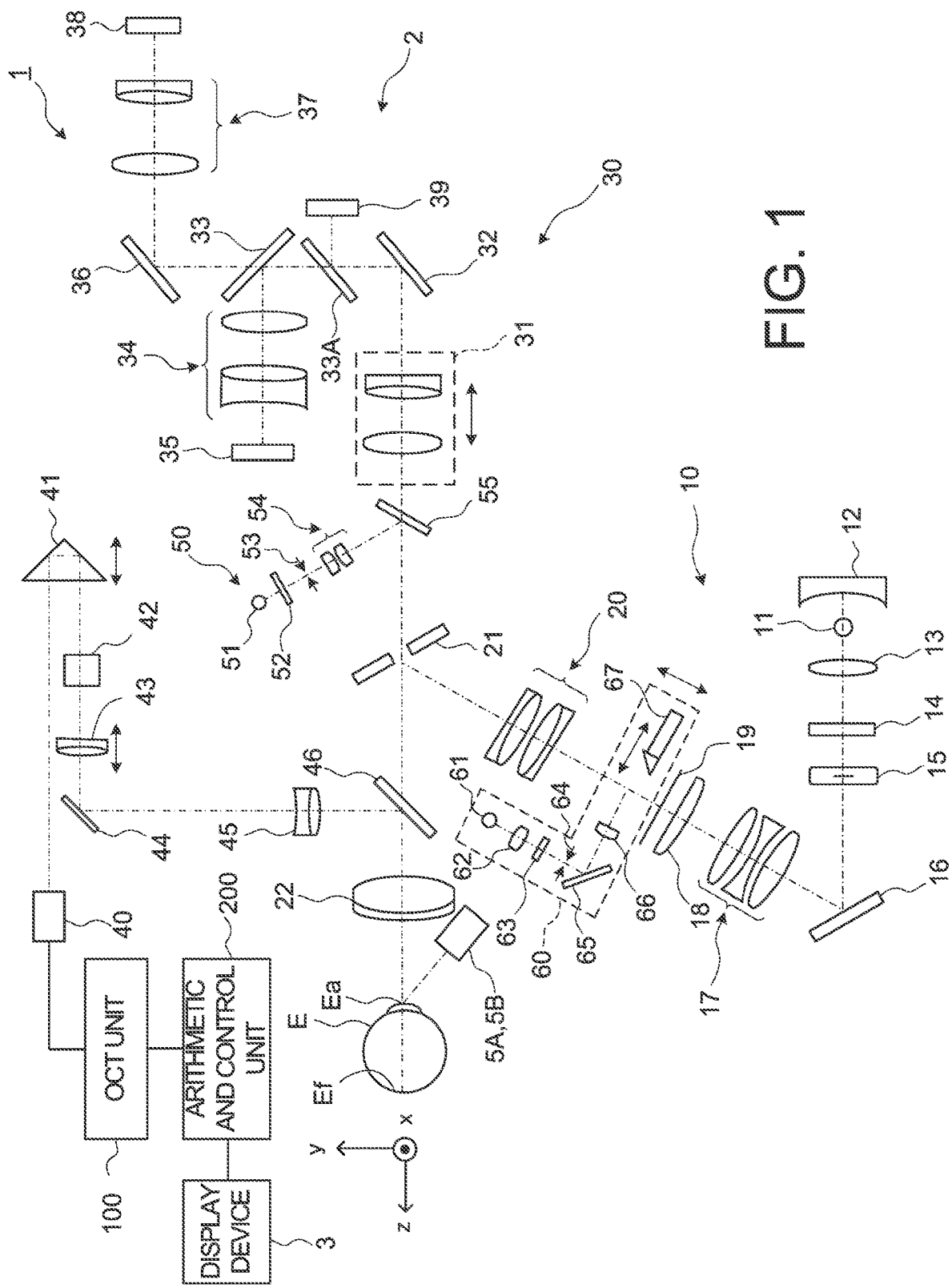
FIG. 1 is a schematic diagram illustrating an example of a configuration of an ophthalmologic apparatus according to embodiments.

In the conventional technique, it is sometimes impossible to remove the flare region depicted in the image of the subject's eye due to alignment errors, placement of the optical elements, or the like.

According to some embodiments of the present invention, a new technique for removing flare region depicted in the image of the subject's eye can be provided.

Referring now to the drawings, exemplary embodiments of an ophthalmologic apparatus and a method of controlling the ophthalmologic apparatus according to some embodiments of the present invention are described below. Any of the contents of the documents cited in the present specification and arbitrary known techniques may be applied to the embodiments below.

The ophthalmologic apparatus according to some embodiments includes an ophthalmologic imaging apparatus. The ophthalmologic imaging apparatus included in the ophthalmologic apparatus according to some embodiments includes any one or more of a fundus camera, a scanning laser ophthalmoscope, a slit lamp microscope, a surgical microscope, and the like, for example. The ophthalmologic apparatus according to some embodiments includes any one or more of an ophthalmologic measuring apparatus and an ophthalmologic therapy apparatus, in addition to the ophthalmologic imaging apparatus. The ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. The ophthalmologic therapy apparatus includes in the ophthalmologic apparatus according to some embodiments includes any one or more of a laser therapy apparatus, a surgical apparatus, a surgical microscope, and the like, for example.

In the following embodiments, the ophthalmologic apparatus according to the embodiments includes an optical coherence tomography (OCT) and a fundus camera. Although swept source OCT is employed as OCT, the type of OCT is not limited to the swept source OCT. It is also possible to employ other types of OCT (spectral domain OCT, time domain OCT, en-face OCT, or the like).

Hereinafter, it is assumed that the x direction is a direction orthogonal to an optical axis direction of an objective lens (left and right direction), and the y direction is a direction orthogonal to the optical axis direction of the objective lens (left and right direction). The z direction is assumed to be the optical axis direction of the objective lens.

<Configuration>
[Optical System]

As shown in FIG. 1, the ophthalmologic apparatus 1 includes a fundus camera unit 2, an OCT unit 100, and an arithmetic and control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic and control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1. Furthermore, the ophthalmologic apparatus 1 includes a pair of anterior segment cameras 5A and 5B.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes the function according to the embodiments, for example, by read out a computer program stored in a storage circuit or a storage device and executing the computer program.

[Fundus Camera Unit 2]

The fundus camera unit 2 is provided with an optical system for imaging a fundus Ef of the subject's eye E. An image (called fundus image, fundus photograph, etc.) of the fundus Ef to be obtained is a front image such as an observation image, a photographic image, and the like. The observation image is obtained by moving image shooting using near infrared light. The photographic image is a still image using flash light. Furthermore, the fundus camera unit 2 can obtain the front image (anterior segment image) by photographing an anterior segment Ea of the subject's eye E.

The fundus camera unit 2 includes an illumination optical system 10 and an imaging optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflection mirror 12 having a curved reflective surface, and becomes near-infrared light after penetrating a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, penetrates a dichroic mirror 46, and is refracted by an objective lens 22, thereby illuminating the subject's eye E (fundus Ef or anterior segment Ea). Returning light of the observation illumination light reflected from the subject's eye E is refracted by the objective lens 22, penetrates the dichroic mirror 46, passes through the hole part formed in the center area of the perforated mirror 21, penetrates a dichroic mirror 55. The returning light penetrating the dichroic mirror 55 travels through a photography focusing lens 31 and is reflected by a mirror 32. Further, this returning light penetrates a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) output from the imaging light source 15 is projected onto the fundus Ef via the same route as that of the observation illumination light. Returning light of the imaging illumination light from the subject's eye E is guided to the dichroic mirror 33 via the same route as that of the observation illumination light, penetrates the dichroic mirror 33, is reflected by a mirror 36, and forms an image on the light receiving surface of the image sensor 38 by a condenser lens 37.

An image (observation image) based on the fundus reflection light detected by the image sensor 35 is displayed on a display device 3. Note that when the imaging optical system 30 is focused on the anterior segment, an observation image of the anterior segment of the subject's eye E is displayed. Furthermore, the display device 3 displays an image (photographic image) based on the fundus reflection light detected by the image sensor 38. Note that the display device 3 for displaying the observation image and the display device 3 for displaying the photographic image may be the same or different. When similar photographing is performed by illuminating the subject's eye E with infrared light, an infrared photographic image is displayed.

A liquid crystal display (LCD) 39 displays a fixation target and a visual target used for visual acuity measurement. Part of light output from the LCD 39 is reflected by the half mirror 33A, is reflected by the mirror 32, travels through the photography focusing lens 31 and the dichroic mirror 55, and passes through the hole part of the perforated mirror 21. The light beam having passed through the hole part of the perforated mirror 21 penetrates the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a position for acquiring an image centered at a macula, a position for acquiring an image centered at an optic disc, a position for acquiring an image centered at the fundus center between the macula and the optic disc, a position for acquiring an image of a site (fundus peripheral part) far away from the macula, and the like. The ophthalmologic apparatus 1 according to some embodiments includes GUI (Graphical User Interface) and the like for designating at least one such the fixation position. The ophthalmologic apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

The alignment optical system 50 generates an alignment indicator for alignment of the optical system with respect to the subject's eye E. Alignment light output from an LED 51 travels through the diaphragms 52 and 53 and the relay lens 54, is reflected by the dichroic mirror 55, and passes through the hole part of the perforated mirror 21. The alignment light having passed through the hole part of the perforated mirror 21 penetrates the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To conduct focus adjustment, the reflective surface of the reflection rod 67 is arranged in a slanted position on the illumination optical path. Focus light output from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, penetrates the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof.

The dichroic mirror 46 combines an optical path for fundus photography and an optical path for OCT. The dichroic mirror 46 reflects light of wavelength band used in OCT, and transmits light for fundus photography. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing part 41 is movable in directions indicated by the arrow in FIG. 1, thereby changing the length of the optical path for OCT. This change in the optical path length is used for correcting the optical path length according to the axial length, adjusting the interference state, or the like. The optical path length changing part 41 includes a corner cube and a mechanism for moving the corner cube.

The optical scanner 42 is disposed at a position optically conjugate with the pupil of the subject's eye E. The optical scanner 42 deflects the measurement light LS traveling along the OCT optical path. The optical scanner 42 is a galvano scanner capable of scanning two-dimensionally, for example.

The OCT focusing lens 43 is moved along the optical path of the measurement light LS to perform focus adjustment of the optical system for OCT. The movement of the photography focusing lens 31, the movement of the focus optical system 60, and the movement of the OCT focusing lens 43 can be controlled in conjunction with each other.

[Anterior Segment Cameras 5A and 5B]

The anterior segment cameras 5A and 5B are used for obtaining relative position between the optical system of the ophthalmologic apparatus 1 and the subject's eye E in the same manner as the invention disclosed in Japanese Unexamined Patent Application Publication No. 2013-248376. The anterior segment cameras 5A and 50B are located on a surface of a housing (fundus camera unit 2 etc.) in which the optical system is stored to face the subject's eye E. The ophthalmologic apparatus 1 obtains the three-dimensional relative position between the optical system and the subject's eye E, by analyzing two anterior segment images acquired substantially simultaneously from different directions by the anterior segment cameras 5A and 5B. The analysis of the two anterior segment images may be the same as the analysis disclosed in Japanese Unexamined Patent Application Publication No. 2013-248376. Furthermore, it should be noted that the number of the anterior segment cameras may be arbitrary (equal to or more than two).

In the present examples, the position of the subject's eye E (that is, the relative position between the subject's eye E and the optical system) is obtained using two or more anterior segment cameras. However, a method of obtaining the position of the subject's eye E is not limited to this. For example, the position of the subject's eye E can be obtained by analyzing the front image (for example, the observation image of the anterior segment Ea) of the subject's eye E. Alternatively, means for projecting an indicator onto the cornea of the subject's eye can be provided. Thereby, the position of the subject's eye E can be obtained based on the projection position of the indicator (that is, the detection state of the corneal reflection light flux of this indicator).

[OCT Unit 100]

Figure 2:
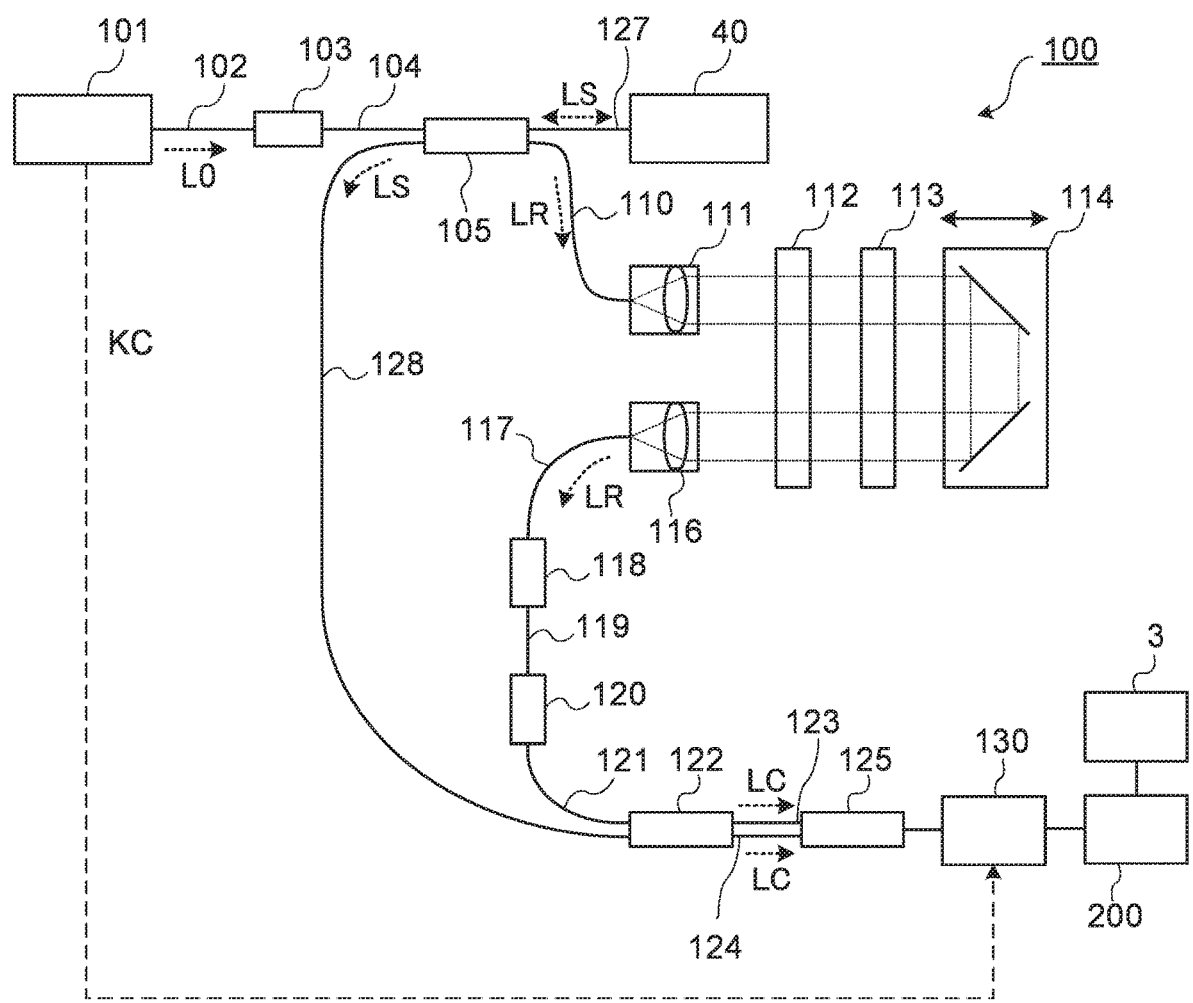
FIG. 2 is a schematic diagram illustrating an example of the configuration of the ophthalmologic apparatus according to the embodiments.

As illustrated by an example in FIG. 2, the OCT unit 100 is provided with an optical system for performing swept source OCT. This optical system includes an interference optical system. This interference optical system has a function that splits light from the wavelength tunable type (wavelength scanning type) light source into measurement light and reference light, a function that makes the returning light of the measurement light from the subject's eye E and the reference light having traveled through a reference optical path interfere with each other and generates interference light, and a function that detects the interference light. The detection result (detection signal) of the interference light obtained by the interference optical system is a signal indicating a spectrum of the interference light, and is sent to the arithmetic and control unit 200.

The light source unit 101 includes a near-infrared tunable laser which changes the wavelength of the emitted light at high speed, for example. Light LO output from the light source unit 101 is guided to the polarization controller 103 by the optical fiber 102, and the polarization state of the light LO is adjusted. The light LO whose polarization state has been adjusted is guided to the fiber coupler 105 through the optical fiber 104. The fiber coupler 105 splits the light LO into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into the parallel light beam travels through the optical path length changing unit 41, the optical scanner 42, the OCT focusing lens 43, the mirror 44, and the relay lens 45. The measurement light LS having traveled through the relay lens 45 is reflected by the dichroic mirror 46, is refracted by the objective lens 22, and is irradiated onto the subject's eye E. The measurement light LS is scattered and reflected at various depth positions of the subject's eye E. Returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC are guided to a detector 125 through optical fibers 123 and 124, respectively.

The detector 125 is a balanced photodiode, for example. The balanced photodiode includes a pair of photodetectors that respectively detect the pair of interference light LC and output the difference between a pair of detection results acquired by the pair of photodetectors. The detector 125 sends the output (detection signal) to a DAQ (data acquisition system) 130.

A clock KC is supplied from the light source unit 101 to the DAQ 130. The clock KC is generated in the light source unit 101 in synchronization with the output timing of each wavelength within a predetermined wavelength range performed by the wavelength tunable type light source. For example, the light source unit 101 optically delays one of the two pieces of branched light obtained by branching the light LO of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic and control unit 200.

In the present examples, both the optical path length changing unit 41 that changes the length of the optical path of the measurement light LS (i.e., measurement optical path or measurement arm) and the corner cube 114 that changes the length of the optical path of the reference light LR (i.e., reference optical path or reference arm) are provided. Alternatively, any one of the optical path length changing unit 41 and the corner cube 114 may be provided. The difference between the measurement optical path length and the reference optical path length can be changed using other optical members.

[Control System]

Figure 3:
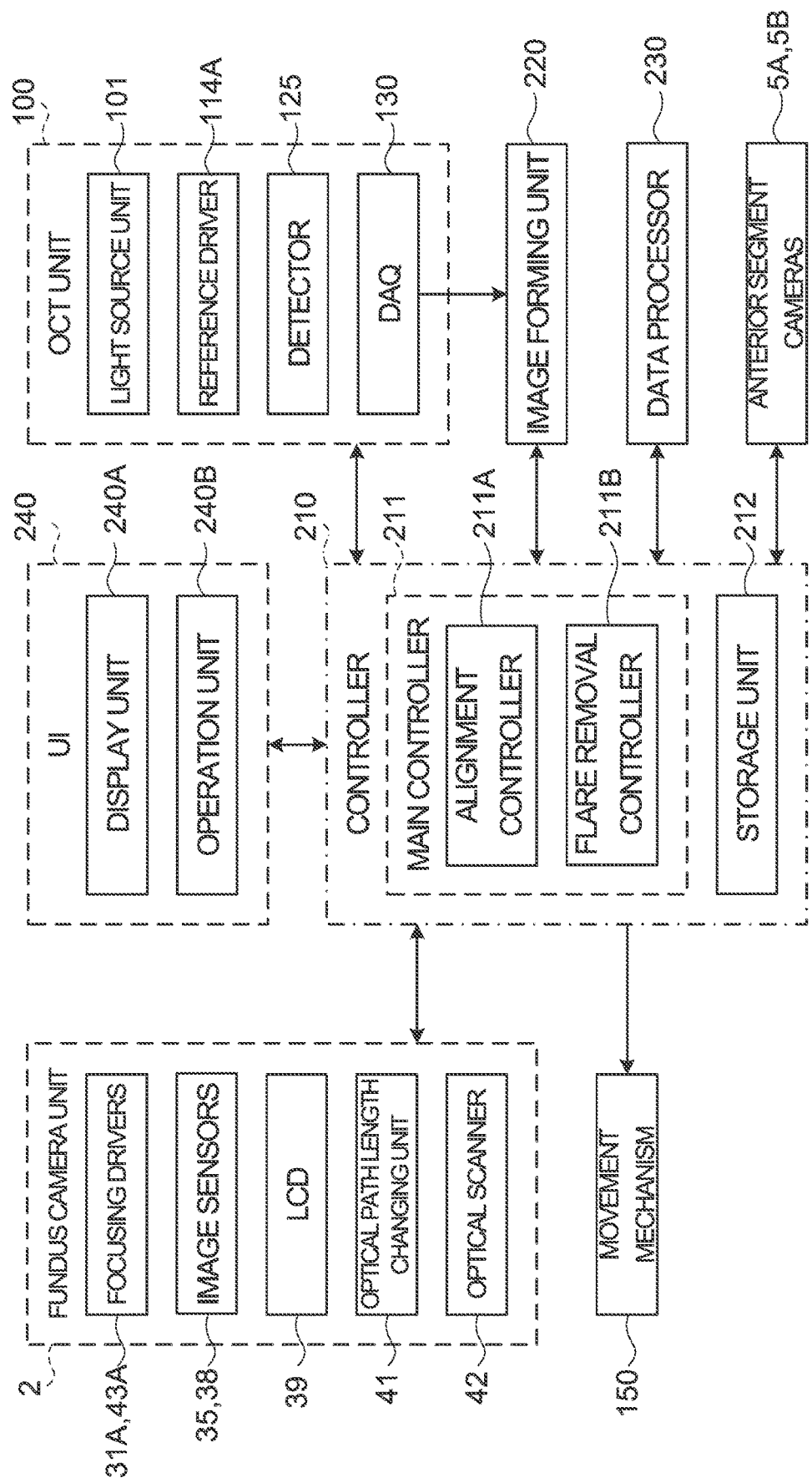
FIG. 3 is a schematic diagram illustrating an example of the configuration of the ophthalmologic apparatus according to the embodiments.
Figure 4:
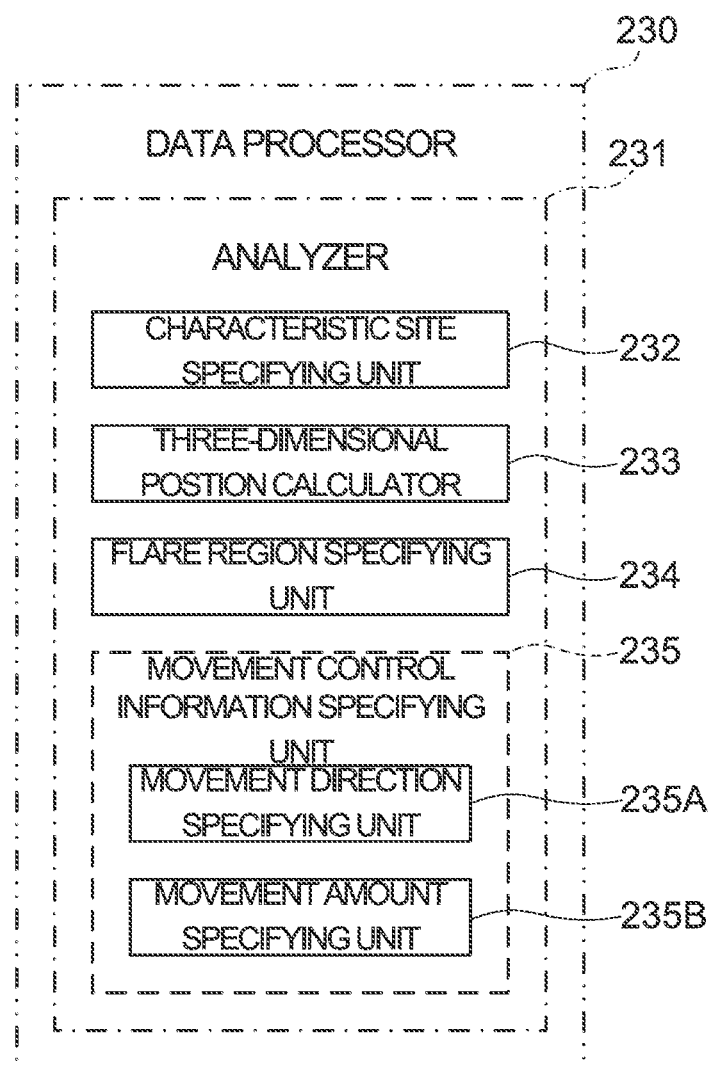
FIG. 4 is a schematic diagram illustrating an example of the configuration of the ophthalmologic apparatus according to the embodiments.

FIGS. 3 and 4 illustrate a configuration example of a control system of the ophthalmologic apparatus 1. In FIGS. 3 and 4, a part of the components included in the ophthalmologic apparatus 1 is omitted. For example, the arithmetic and control unit 200 is provided with a controller 210, an image forming unit 220, and a data processor 230.

<Controller 210>

The controller 210 executes various controls. The controller 210 includes a main controller 211 and a storage unit 212.

<Main Controller 211>

The main controller 211 includes a processor (for example, control processor) and controls each part (including each element show in FIGS. 1 to 4) of the ophthalmologic apparatus 1. For example, the main controller 211 controls a photography focusing driver 31A to move the photography focusing lens 31. Furthermore, the main controller 211 controls an OCT focusing driver 43A to move the OCT focusing lens 43. In addition, the main controller 211 controls a reference driver 114A to move the corner cube 114.

The main controller 201 includes an alignment controller 211A and a flare removal controller 211B. The alignment controller 211A controls the movement mechanism 150 as described after, thereby performing the position matching of the optical system with respect to the subject's eye E. The flare removal controller 211B controls the movement mechanism 150 based on movement control information specified by analyzing the image of the fundus Ef of the subject's eye E as described after, thereby removing a flare region depicted in the image of the fundus Ef.

The movement mechanism 150 three-dimensionally moves at least the fundus camera unit 2 (optical system), for example. In a typical example, the movement mechanism 150 includes a mechanism for moving at least the fundus camera unit 2 in the x direction (left and right direction), a mechanism for moving it in the y direction (vertical direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes a pulse motor as an actuator and operates under the control of the alignment controller 211A (main controller 211).

In the case of manual alignment, a user operates a user interface (UI) 240 described after to relatively move the optical system and subject's eye E so as to cancel the displacement of the subject's eye E with respect to the optical system. For example, the alignment controller 211A controls the movement mechanism 150 to relatively move the optical system with respect to the subject's eye E by outputting a control signal corresponding to the operation content with respect to the user interface 240 to the movement mechanism 150.

In the case of automatic alignment, the alignment controller 211A controls the movement mechanism 150 to relatively move the optical system with respect to the subject's eye E so as to cancel the displacement of the subject's eye E with respect to the optical system. In some embodiments, the alignment controller 211A controls the movement mechanism 150 to relatively move the optical system with respect to the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 controls the LCD 39. For example, the main controller 211 controls the LCD 39 to display the fixation target at a position on the screen of the LCD 39 corresponding the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 230, for example.

The main controller 211 (flare removal controller 211B) controls the movement mechanism 150 to relatively move the optical system with respect to the subject's eye E, so as to remove the flare region represented in the acquired image (image of the fundus Ef) of the subject's eye E. The flare region is a region in which an image formed based on reflected light other than fundus reflection light is drawn in the image formed by receiving the reflected light. The flare removal controller 211B controls the movement mechanism 150 using relative movement direction and relative movement amount obtained by analyzing the flare region. In some embodiments, the flare removal controller 211B controls the movement mechanism 150 using the relative movement direction and the relative movement amount specified based on a change in the flare region before and after the relative movement of the optical system with respect to the subject's eye E. Thereby, the flare due to alignment error, displacement of optical elements, or the like can be removed with high accuracy and quickly in addition to when the subject's eye is directed obliquely due to the heterophoria or the like, when the cornea is distorted due to the disease of the cornea or the like, or when the subject's eye is a small pupil.

(Storage Unit 212)

The storage unit 212 stores various types of data. Examples of the data stored in the storage unit 212 include, for example, data of the subject's eye E such as OCT data, OCT images, fundus images, and anterior segment images which are acquired using OCT unit 100, and subject's eye information. The subject's eye information includes information on the subject such as patient ID and name, information on the subject's eye such as identification information of the left eye/right eye, information of electronic medical record. The storage unit 212 further may store various types of programs for executing various processors (control processor, image forming processor, data processing processor).

<Image Forming Unit 220>

The image forming part 220 includes a processor (image forming processor, for example) and forms an image based on the output (sampling result of the detection signals) from the DAQ 130. For example, the image forming unit 220 forms a reflection intensity profile for each A line by applying signal processing to the spectral distribution on the basis of the sampling detection for each A line in the same manner as in the conventional swept source OCT, images these A line profiles, and arranges them along the scan line. The above signal processing includes noise removal (noise reduction), filtering, fast Fourier transform (FFT), and the like.

<Data Processor 230>

The data processor 230 includes a processor (data processing processor, for example) and performs various kinds of image processing and various kinds of analysis processing on the image formed by the image forming unit 220. At least two of the processor included in the main controller 211, the processor included in the data processor 230, and the processor included in the image forming unit 220 may be configured by a single processor. The data processor 230 includes an analyzer 231.

<Analyzer 231>

The analyzer 231 analyzes the image (image of the anterior segment Ea, for example) of the subject's eye E, specifies a characteristic site represented in the image, and obtains a three-dimensional position of the subject's eye E based on the positions of the anterior segment cameras 5A and 5B and the specified position of the characteristic site. The alignment controller 211A performs position matching of the optical system with respect to the subject's eye E, by relatively moving the optical system with respect to the subject's eye E based on the obtained three-dimensional position.

Furthermore, the analyzer 231 analyzes the image (fundus image) of the fundus Ef of the subject's eye E, specifies the flare region depicted in the image, and obtains the relative movement direction of the optical system with respect to the subject's eye E and the relative movement amount of the optical system with respect to the subject's eye E based on the specified flare region. After position matching of the optical system with respect to the subject's eye E is completed, the flare removal controller 211B removes the flare region depicted in the image by relatively moving the optical system with respect to the subject's eye E based on the obtained relative movement direction and the obtained relative movement amount.

The analyzer 231 includes a characteristic site specifying unit 232, a three-dimensional position calculator 233, a flare region specifying unit 234, and a movement control information specifying unit 235. The movement control information specifying unit 235 includes a movement direction specifying unit 235A and a movement amount specifying unit 235B.

<Characteristic Site Specifying Unit 232>

The characteristic site specifying unit 232 analyzes each photographic images captured by the anterior segment cameras 5A and 5B to specify the position (called characteristic position) in the photographic image corresponding to the characteristic site of the anterior segment Ea. Examples of the characteristic site includes a pupil region of the subject's eye E, a center position of the pupil of the subject's eye E, a position of the center of gravity of the pupil, a center position of the cornea, a position of the corneal apex, a center position of the subject's eye, and an iris. In the following, a specific example of a process for specifying the center position of the pupil of the subject's eye E is explained.

First, the characteristic site specifying part 232 specifies an image region (pupil region) corresponding to the pupil of the subject's eye E based on the distribution of pixel values (luminance values etc.) in the photographic image. Generally, the pupil is represented with lower luminance compared to other sites, and therefore, the pupil region may be specified by searching an image region with low luminance. At this time, the pupil region may be specified by taking the shape of the pupil into consideration. That is, it is possible to configure such that the pupil region is specified by searching for a substantially circular image region with low luminance.

Next, the characteristic site specifying unit 232 specifies the center position of the specified pupil region. As mentioned above, the pupil is substantially circular; therefore, it is possible to specify the contour of the pupil region, to specify the center position of this contour (an approximate circle or an approximate ellipse thereof), and to treat this as the center of the pupil. Instead, by obtaining the center of gravity of the pupil region, this position may be used as the position of the center of gravity of the pupil.

It should be noted that even when specifying the characteristic position corresponding to other characteristic site, it is possible to specify the characteristic position based on the pixel value distribution of the photographic image in the same manner as those mentioned above.

The characteristic site specifying unit 232 can sequentially specify a characteristic position corresponding to a characteristic site of each photographic image sequentially obtained by the anterior segment cameras 5A and 5B. Moreover, the characteristic site specifying unit 232 may specify the characteristic position for each photographic image sequentially obtained by the anterior segment cameras 5A and 5B every any number (one or more) of frames.

<Three-Dimensional Position Calculator 233>

The three-dimensional position calculator 233 specifies a three-dimensional position of the characteristic site as the three-dimensional position of the subject's eye E based on the positions of the anterior segment cameras 5A and 5B and the characteristic position corresponding to the characteristic site specified by the characteristic site specifying unit 232. The three-dimensional position calculates 233 calculates the three-dimensional position of the subject's eye E by applying known trigonometry to the positions of the two anterior segment cameras 5A and 5B (these are known) and the positions corresponding to the characteristic site in two photographic images, as disclosed in Japanese Unexamined Patent Application Publication No. 2013-248376. The three-dimensional position calculated by the three-dimensional position calculator 233 is sent to the alignment controller 211A. The alignment controller 211A controls the movement mechanism 150 based on the three-dimensional position so that the position of the optical axis of the optical system in the x and the y directions respectively coincide with the position of the three-dimensional position in the x and the y directions and the distance in the z direction becomes a predetermined working distance.

<Flare Region Specifying Unit 234>

The flare region specifying unit 234 specifies the flare region depicted in the image (fundus image) of the fundus Ef by analyzing the photographic image acquired by the imaging optical system 30. For example, the characteristic site specifying unit 234 specifies an image region depicted at the edge (peripheral) part or the like of the fundus region based on the distribution of pixel values (luminance values etc.) in the photographic image. Generally, the flare region is represented as a region where the luminance value is saturated, and therefore, the flare region may be specified by searching an image region with a luminance value equal to a saturation value of the luminance value or a luminance value equal to or higher than a threshold value close to the saturation value. At this time, the flare region may be specified by taking the depicted position of the flare region into consideration. For example, considering that the shape of the flare region depicted at the edge part of the fundus region is a crescent shape, the flare region can be specified by searching the image region having a crescent shape with a luminance value equal to the saturation value or a luminance value equal to or higher than the threshold value close to the saturation value.

The flare region specifying unit 234 can specify a representative position of the specified flare region. Examples of the representative position include a position of the center of gravity, a center position, a center position of an inscribed circle of the flare region, a center position of a circumscribed circle of the flare region, and the like. In the following, a specific example of a process for specifying the position of the center of gravity of the flare region is explained. By adopting the position of the center of gravity as the representative position of the flare region, a plurality of the flare regions formed at the edge part of the fundus region can be removed when the optical system is relatively moved with respect to the subject's eye E in a single direction.

For example, the flare region specifying unit 234 performs pre-processing such as binarization processing to the specified flare region, and then specifies the position of the center of gravity based on the distribution of pixel values of the flare region using a known image moment. That is, the position of the center of gravity in the x direction is obtained by normalizing the first moment in the x direction with the zero-order moment. In the same manner, the position of the center of gravity in the y direction is obtained by normalizing the first moment in the y direction with the zero-order moment.

Furthermore, the flare region specifying unit 234 may obtain a contour of the specified flare region and may specify the position of the center of gravity from the obtained contour using a known method.

<Movement Control Information Specifying Unit 235>

The movement control information specifying unit 235 specifies at least one of the relative movement direction and the relative movement amount of the optical system with respect to the subject's eye E, based on the flare region specified in the image of the fundus Ef of the subject's eye E and a reference position in the image. Examples of the reference position in the image include a center position of the image and the like.

<Movement Direction Specifying Unit 235A>

The movement direction specifying unit 235A specifies the relative movement direction of the optical system with respect to the subject's eye E by the movement mechanism 150. The relative movement direction corresponds to a driving direction of the optical system by the movement mechanism 150. For the first (initial) relative movement of the optical system with respect to the subject's eye E, the movement direction specifying unit 235A specifies the relative movement direction based on the center position of the image of the fundus Ef and the position of the center of gravity of the flare region specified by the flare region specifying unit 234.

Figure 5A:
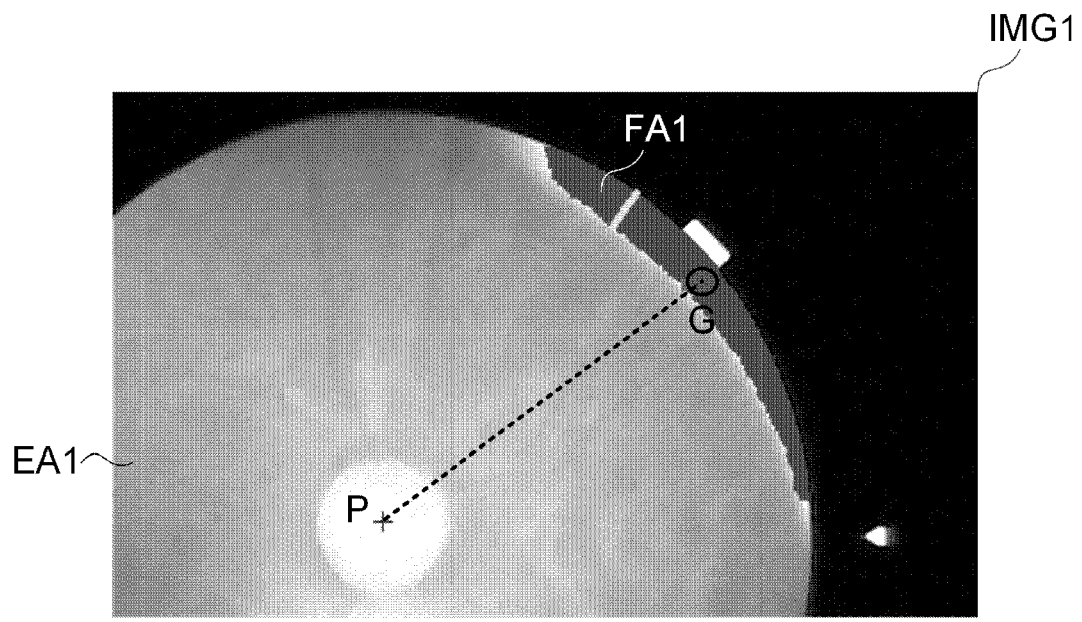
FIG. 5A is a schematic diagram for explaining an operation of the ophthalmologic apparatus of the embodiments.
Figure 5B:
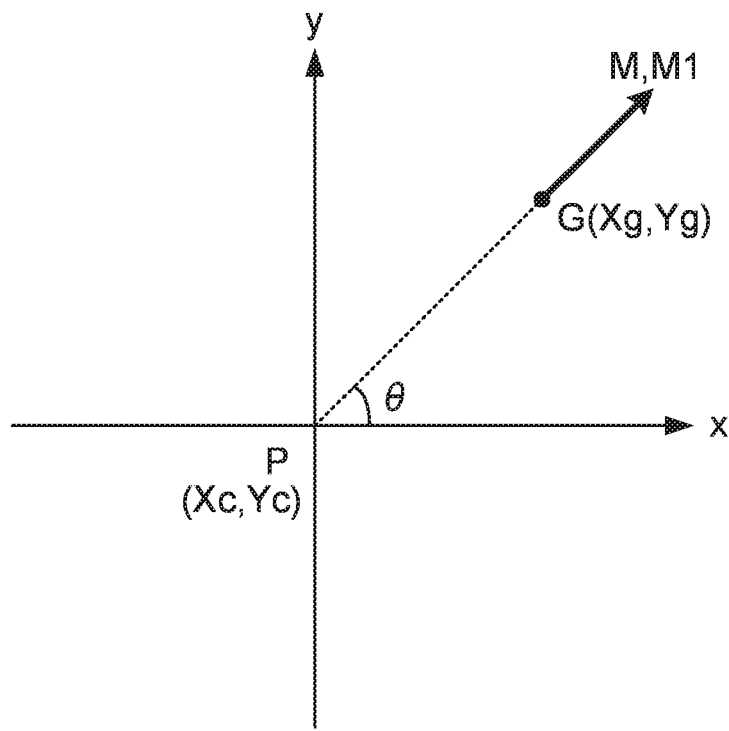
FIG. 5B is a schematic diagram for explaining an operation of the ophthalmologic apparatus of the embodiments.

FIGS. 5A and 5B show diagrams describing the operation of the movement direction specifying unit 235A according to the embodiments. FIG. 5A illustrates an example of the fundus image IMG1 acquired using the imaging optical system 30. In the fundus image IMG1, a flare region FA1 is depicted at the edge part of the fundus region EA1. The center position of the fundus image IMG1 is assumed to substantially coincide with the center position of the fundus region EA1. FIG. 5B schematically illustrates the relative movement direction specified based on the center position P of the fundus image IMG1 and the position G of the center of gravity of the flare region FA1.

It is assumed that the coordinate position of the center position P of the fundus image IMG1 is (Xc, Yc), the coordinate position of the position G of the center of gravity of the flare region FA1 is (Xg, Yg), and an angle formed by a straight line, which connects the center position P and the position G of the center of gravity, and the x axis is θ. The movement direction specifying unit 235A specifies a direction toward the position G of the center of gravity from the center position P as the relative movement direction of the optical system with respect to the subject's eye E. Specifically, the movement direction specifying unit 235A obtains the angle θ representing the relative movement direction as shown in Expression (1).

$$\theta = \mathrm{atan}((Yg-Yc)/(Xg-Xc)) \quad (1)$$

That is, the flare removal controller 211B relatively moves the optical system with respect to the subject's eye E in the direction having the angle θ with respect to the x direction and toward the position G of the center of gravity from the center position P.

<Movement Amount Specifying Unit 235B>

The movement amount specifying unit 235B specifies the relative movement amount of the optical system with respect to the subject's eye E by the movement mechanism 150. The relative movement amount corresponds to driving amount of the optical system by the movement mechanism 150.

For the first relative movement of the optical system with respect to the subject's eye E, the movement amount specifying unit 235B outputs predetermined movement amount (predetermined amount). When it is determined that the flare region is not removed by the first relative movement, the movement amount specifying unit 235B outputs the relative movement amount corresponding to the change (direction of change, amount of change) in the flare region before and after the relative movement of the optical system with respect to the subject's eye E by the movement mechanism 150 for the second and subsequent relative movements.

In some embodiments, the relative movement amount output for the first relative movement is alignment error amount of automatic alignment (or manual alignment). When the alignment error amount of automatic alignment is e0 (um) and the movement amount of the movement mechanism 150 driven by the pulse motor is d0 (um/pulse), the movement amount specifying unit 235B specifies (e0/d0) (pulse) as a predetermined relative movement amount M. e0 and d0 are known.

Specifically, for the first relative movement, the movement amount specifying unit 235B obtains the relative movement amount Mx in the x direction and the relative movement amount My in the y direction as shown in expressions (2) and (3). And the movement amount specifying unit 235B outputs [Mx] (pulse) or [Mx]+1 (pulse) as the relative movement amount in the x direction and outputs [My] (pulse) or [My]+1 (pulse) as the relative movement amount in the y direction. Here, [d] means the largest integer not exceeding the real number d.

$$Mx = M \times \cos\theta \quad (2)$$

$$My = M \times \sin\theta \quad (3)$$

In some embodiments, on the condition that the change amount (decrease amount) in the size of the flare region is proportional to the relative movement amount of the optical system with respect to the subject's eye E, the relative movement amount output for the second and subsequent relative movements corresponds to the change in the flare region before and after the movement. The relative movement amount to be removed the flare region can be theoretically specified from the size of the flare region after the relative movement. The movement amount specifying unit 235B specifies the relative movement amount for removing the flare region after the latest relative movement based on the size of the flare region after the relative movement and the predetermined relative movement amount M. In some embodiments, the size (flare amount) of the flare region corresponds to the length of the longest portion (portion representing the thickness of the flare region) in the radial direction centered on the reference position (center position)

of the fundus image. In some embodiments, for the second and subsequent relative movements, the movement amount specifying unit 235B specifies the relative movement amount so as not to increase the flare region in a direction opposite to the relative movement direction.

Figure 6A:
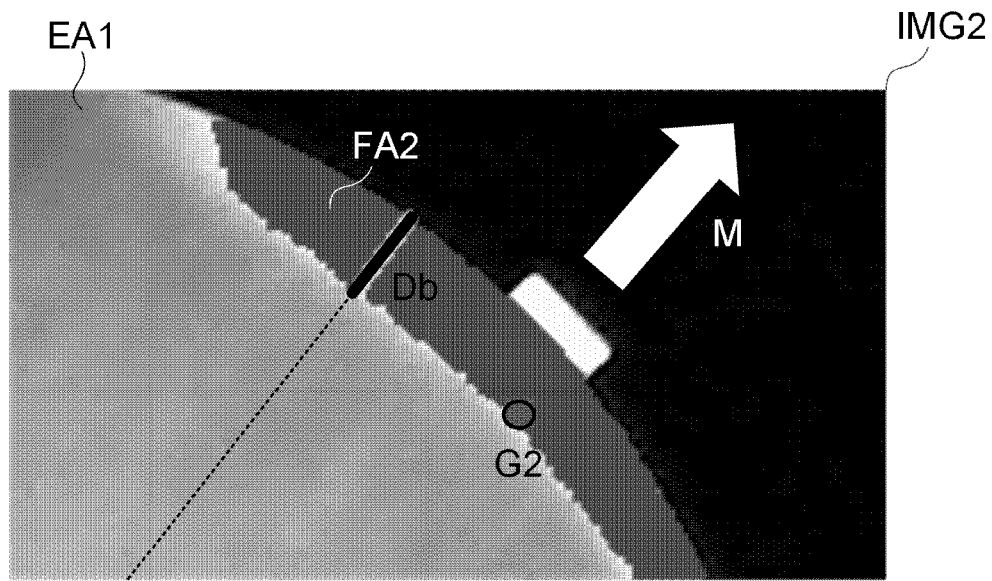
FIG. 6A is a schematic diagram for explaining an operation of the ophthalmologic apparatus of the embodiments.
Figure 6B:
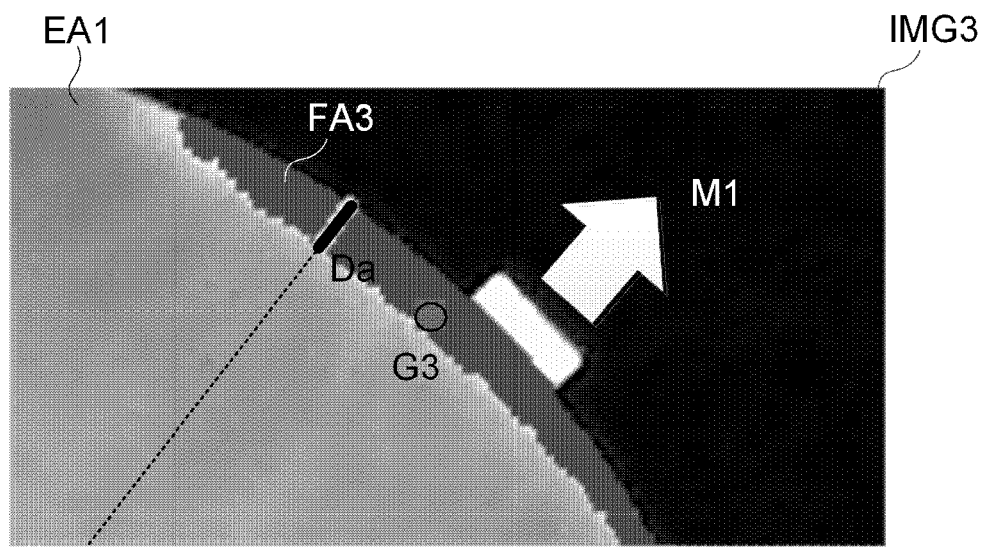
FIG. 6B is a schematic diagram for explaining an operation of the ophthalmologic apparatus of the embodiments.
Figure 6C:
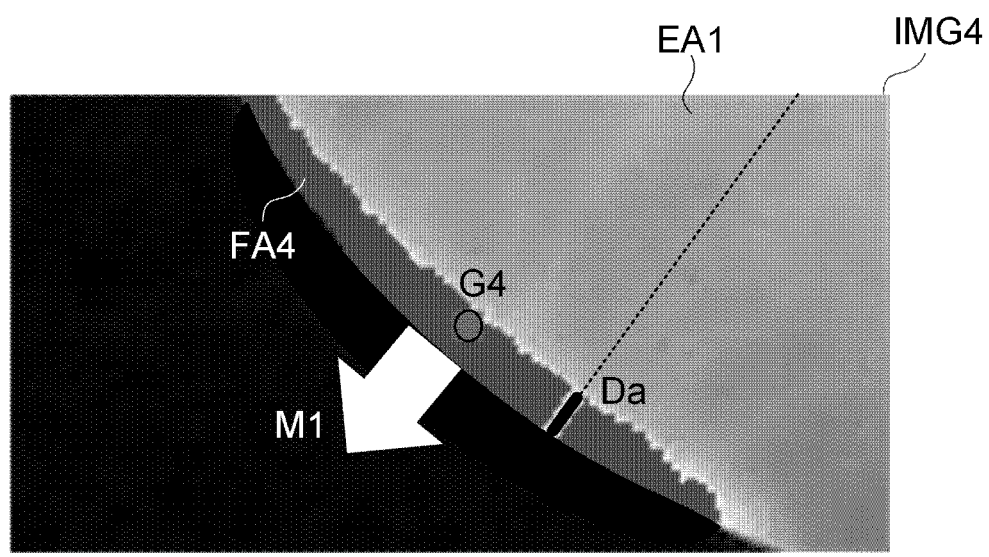
FIG. 6C is a schematic diagram for explaining an operation of the ophthalmologic apparatus of the embodiment.

FIGS. 6A to 6C show diagrams describing the operation of the movement amount specifying unit 235B according to the embodiments. FIG. 6A illustrates an enlarged drawing of an example of the flare region depicted in the fundus image before the first relative movement. FIG. 6B illustrates an enlarged drawing of an example of the flare region depicted in the fundus image after the first relative movement. FIG. 6C schematically illustrates the flare region in the case where the flare region increases in the direction opposite to the relative movement direction after the first relative movement.

In the fundus image IMG2 acquired before the first relative movement, a flare region FA2 is depicted at the edge part of the fundus region EA1 as shown in FIG. 6A. The position of the center of gravity of the flare region FA2 is G2. It is assumed that the longest portion in the radial direction centered on the center position of the fundus image IMG2 in the flare region FA2 is db.

In the fundus image IMG3 (IMG4) acquired after the first relative movement, a flare region FA3 (FA4) is depicted at the edge part of the fundus region EA1 as shown in FIG. 6B (FIG. 6C). The position of the center of gravity of the flare region FA3 (FA4) is G3 (G4). It is assumed that the longest portion in the radial direction centered on the center position of the fundus image IMG3 (IMG4) in the flare region FA3 (FA4) is Da.

When the coordinate position of the start point of the longest portion in the radial direction of the flare region FA2 is (X1s, Y1s) and the coordinate position of the end point is (X1e, Y1e), the radial length db (um) shown in FIG. 6A is represented in expression (4).

[Equation 1]

$$db = \sqrt{(X1e-X1s)^2 + (Y1e-Y1s)^2} \quad (4)$$

In the same manner, when the coordinate position of the start point of the longest portion in the radial direction of the flare region FA3 is (X2s, Y2s) and the coordinate position of the end point is (X2e, Y2e), the radial length Da (um) shown in FIG. 6B is represented in expression (5).

[Equation 2]

$$Da = \sqrt{(X2e-X2s)^2 + (Y2e-Y2s)^2} \quad (5)$$

Here, a detection flag in the direction which the flare region increases (generates) in the direction opposite to the relative movement direction as shown in FIG. 6C is v. It is assumed that v becomes "−1" when both the expressions (6) and (7) are satisfied and v becomes "+1" when the expression (6) or (7) is not satisfied.

$$(X1g-Xc) \times (X2g-Xc) < 0 \quad (6)$$

$$(Y1g-Yc) \times (Y2g-Yc) < 0 \quad (7)$$

Flare amount D' (um/pulse) that the pulse motor included in the movement mechanism 150 can remove with one pulse is represented in the expression (8).

$$D' = (db - (v \times Da))/M \quad (8)$$

Therefore, the relative movement amount M1 necessary for removing the remaining flare region after the relative movement can be obtained from (Da/D').

Specifically, for the second and subsequent relative movements, the movement amount specifying unit 235B obtains the relative movement amount M1x in the x direction and the relative movement amount M1y in the y direction as shown in expressions (9) and 10). And the movement amount specifying unit 235B outputs [M1x] (pulse) or [M1x]+1 (pulse) as the relative movement amount in the x direction and outputs [M1y] (pulse) or [M1y]+1 (pulse) as the relative movement amount in the y direction.

$$M1x = M1 \times \cos\theta \quad (9)$$

$$M1y = M1 \times \sin\theta \quad (10)$$

<User Interface 240>

A user interface 240 includes a display unit 240A and an operation unit 240B. The display unit 240A includes the display device 3. The operation unit 240B includes various operation devices and input devices.

The user interface 240 may include a device having the output function and the input function integrated together, such as a touch panel display, for example. In another embodiment, at least a part of the user interface 240 may not be included in the ophthalmologic apparatus. For example, the display device may be an external device connected to the ophthalmologic apparatus.

For example, the imaging optical system 30, the optical system from the OCT unit 100 to the objective lens 22, or the optical system mounted on the fundus camera unit 2 is an example of the "data acquisition unit" according to the embodiments. For example, the imaging optical system 30 or the optical system form the OCT unit 100 to the objective lens 22 is an example of the "image acquisition unit" according to the embodiments.

<Operation>

Described below is an example of the operation of the ophthalmologic apparatus 1.

FIG. 7 shows an example of the operation of the ophthalmologic apparatus 1 according to the embodiments. FIG. 7 shows a flow chart of an operation example in the case that the ophthalmologic apparatus 1 performs the flare removal processing after automatic alignment and automatic focus are completed, and then start performing OCT measurement.

(S1: Perform Rough Alignment)

First, the ophthalmologic apparatus 1 performs rough alignment. Specially, the main controller 211 (alignment controller 211A) controls the anterior segment cameras 5A and 5B to substantially simultaneously photograph the anterior segment Ea of the subject's eye E. The characteristic site specifying unit 232 analyzes a pair of the anterior segment images acquired substantially simultaneously by the anterior segment cameras 5A and 5B to specify the pupil center position of the subject's eye E as the characteristic site. The three-dimensional position calculator 233 obtains the three-dimensional position of the subject's eye E. This processing includes arithmetic processing using a trigonometric method based on the positional relationship between a pair of the anterior segment cameras 5A and 5B and the subject's eye E, as described in Japanese Unexamined Patent Application Publication No. 2013-248376, for example.

The main controller 211 controls the movement mechanism 150 based on the three-dimensional position of the subject's eye E obtained by the three-dimensional position calculator 233 so that the optical system (for example, the fundus camera unit 2) and the subject's eye E have a predetermined positional relationship. Here, the predetermined positional relationship is a positional relationship in which photographing and inspection of the subject's eye E can be performed using the optical system. In a typical example, when the three-dimensional position (x coordinate position, y coordinate position, z coordinate position) of the subject's eye E is obtained by the three-dimensional position calculator 233, the position, where the x coordinate position of the optical axis of the objective lens 22 coincides with the x coordinate position of the subject's eye E and the y coordinate position of the optical axis of the objective lens 22 coincides with the y coordinate position of the subject's eye E and a distance between the z coordinate position of the objective lens 22 (front lens surface) and the z coordinate position of the subject's eye E (corneal surface) equals to a predetermined distance (working distance), is set as the movement destination of the optical system.

(S2: Perform Automatic Alignment)

Next, the ophthalmologic apparatus 1 starts performing automatic alignment. The automatic alignment is performed using a pair of the anterior segment cameras 5A and 5B or the alignment indicator in the same manner as in the conventional method.

(S3: Perform Automatic Focus)

Subsequently, the ophthalmologic apparatus 1 starts performing automatic focus. For example, the main controller 211 controls the focus optical system 60 to project the split indicator onto the subject's eye E. The analyzer 231 analyzes the observation image of the fundus Ef onto which the split indicator is projected to extract a pair of split indicator images, and calculates the relative displacement of the pair of the split indicators. The main controller 211 controls the photography focusing driver 31A and the OCT focusing driver 43A based on the calculated displacement (displacement direction, displacement amount).

(S4: Remove Flare Region)

When the automatic focusing is completed, the ophthalmologic apparatus 1 performs flare region removal processing. The flare region removal processing is described in detail later.

In some embodiments, after the automatic focus is completed, a countdown (for example, 5 seconds) to start the OCT measurement (photographing) is started. Step S4 is executed until immediately before the start of the OCT measurement. For example, the flare region removal is performed between the time T0 after starting the countdown and the time T0+ΔT before starting the OCT measurement. It should be noted that step S4 may be executed after time designated in advance has elapsed after starting the countdown.

(S5: Perform OCT Measurement)

Next, the main controller 211 controls the optical scanner 42 and the OCT unit 100 to start performing the OCT measurement. When the OCT measurement is started, the OCT unit 100 sends data collected for each scan to the image forming unit 220. The image forming unit 220 forms a plurality of B scan images from the data collected for each scan and sends them to the controller 210. The controller 210 sends the plurality of B scan images corresponding to each scan to the data processor 230. For example, the data processor 230 forms a three-dimensional image from the plurality of B scan images corresponding to each scan. This terminates the operation of the ophthalmologic apparatus 1 (END).

FIG. 8 illustrates a flow of an example of the operation of step S4 in FIG. 7.

(S41: Obtain Fundus Image)

First, the main controller 211 (flare removal controller 211B) controls the imaging optical system 30 to obtain the image (fundus image) of the fundus Ef of the subject's eye E. In step S41, the fundus image before the relative movement is obtained.

(S42: Specify Flare Region)

Next, the main controller 211 controls the flare region specifying unit 234 to specify the flare region depicted at the edge part of the fundus region in the fundus image obtained in step S41. The flare region specifying unit 234 executes processing for specifying the flare region based on the luminance value of the fundus image as described above.

(S43: Specification Succeeded?)

The main controller 211 determines whether or not the flare region is specified in step S42. The main controller 211 can determine whether or not the flare region is specified based on the flare region specification result by the flare region specifying unit 234.

When it is determined that the flare region is specified (S43: Y), the operation of the ophthalmologic apparatus 1 moves to step S44. When it is determined that the flare region is not specified (S43: N), the flare region removal processing is terminated (END).

(S44: Specify Relative Movement Direction)

When it is determined that the flare region is specified (S43: Y), the main controller 211 controls the movement direction specifying unit 235A to specify the relative movement direction of the optical system with respect to the subject's eye E by the movement mechanism 150. The movement direction specifying unit 235A specifies the relative movement direction for the first relative movement as shown in the expression (1), based on the center position of the fundus image obtained in step S41 and the position of the center of gravity of the flare region specified in step S42 as shown in FIGS. 5A and 5B.

(S45: Move Relatively by Predetermined Amount)

Subsequently, the main controller 211 controls the movement amount specifying unit 235B to specify the relative movement amount of the optical system with respect to the subject's eye E by the movement mechanism 150. The movement amount specifying unit 235B specifies the predetermined relative movement amount M(=e0/d0) for the first relative movement as described above, and outputs the movement control information corresponding to the relative movement amount [Mx] (or [Mx]+1) in the x direction and the relative movement amount [My] (or [My]+1) in the y direction as shown in the expressions (2) and (3). The main controller 211 controls the movement mechanism 150 based on the movement control information to relatively move the optical system with respect to the subject's eye E.

(S46: Obtain Fundus Image)

Again, the main controller 211 controls the imaging optical system 30 to obtain the image (fundus image) of the fundus Ef of the subject's eye E. In step S46, the fundus image after the relative movement is obtained.

(S47: Specify Flare Region)

Subsequently, the main controller 211 controls the flare region specifying unit 234 to specify the flare region depicted at the edge part of the fundus region in the fundus image obtained in step S46. The flare region specifying unit 234 executes processing for specifying the flare region in the same manner as in step S42.

(S48: Specification Succeeded?)

The main controller 211 determines whether or not the flare region is specified in step S47. The main controller 211 can determine whether or not the flare region is specified in the same manner as in step S43.

When it is determined that the flare region is specified (S48: Y), the operation of the ophthalmologic apparatus 1 moves to step S39. When it is determined that the flare region is not specified (S48: N), the flare region removal processing is terminated (END).

(S49: Analyze Flare Region)

When it is determined that the flare region is specified in step S48 (S48: Y), the main controller 211 controls the analyzer 231 to analyze the flare region specified in step S48. The analyzer 231 (flare region specifying unit 234) specifies the change (change amount, change direction) in the size of the flare region before and after the relative movement. The analyzer 231 specifies the change in the size of the flare region based on the length of the longest portion in the radial direction centered on the center position of the fundus image in the flare region as described above.

(S50: Removal of Flare Region Completed?)

The main controller 211 determines whether or not the removal of the flare region after the relative movement is completed. The main controller 211 can determine whether or not the removal of the flare region is completed, based on the size of the flare region obtained from the analysis result by the analyzer 231. For example, the main controller 211 determines that the removal of the flare region is completed when the size of the flare region becomes equal to or less than a predetermined threshold value, and determines that the removal of the flare region is not completed when the size of the flare region exceeds the predetermined threshold value.

When it is determined that the removal of the flare region is completed (S50: Y), the flare region removal processing is terminated (END). When it is determined that the removal of the flare region is not completed (S50: N), the operation of the ophthalmologic apparatus 1 moves to step S51.

(S51: Specify Relative Movement Direction)

When it is determined that the removal of the flare region is not completed (S50: N), the main controller 211 controls the movement direction specifying unit 235A to specify the relative movement direction of the optical system with respect to the subject's eye E by the movement mechanism 150. The movement direction specifying unit 235A specifies the relative movement direction for the second and subsequent relative movements as shown in the expression (1), based on the center position of the fundus image obtained in step S46 and the position of the center of gravity of the flare region specified in step S47 as shown in FIGS. 5A and 5B.

(S52: Specify Relative Movement Amount)

Subsequently, the main controller 211 controls the movement amount specifying unit 235B to specify the relative movement amount of the optical system with respect to the subject's eye E by the movement mechanism 150. The movement amount specifying unit 235B specifies the relative movement amount M1 (=Da/D') for the second and subsequent relative movements as described above, and outputs the movement control information corresponding to the relative movement amount [M1$x$] (or [M1$x$]+1) in the x direction and the relative movement amount [M1$y$] (or [M1$y$]+1) in the y direction as shown in the expressions (9) and (10).

(S53: Move Relatively)

The main controller 211 controls the movement mechanism 150 based on the movement control information output in step S52 to relatively move the optical system with respect to the subject's eye E. The operation of the ophthalmologic apparatus 1 moves to step S46.

In the above embodiments, the case has been described in which the flare region removal processing is performed before starting the OCT measurement; however, the configuration of the ophthalmologic apparatus according to the embodiments is not limited thereto. In some embodiments, the flare region removal processing according to the embodiments is performed before color fundus photographing or peripheral photographing.

In the above embodiments, the case has been described in which steps S51 to S53 in FIG. 8 are repeatedly executed until it is determined the flare region is removed; however, the configuration of the ophthalmologic apparatus according to the embodiments is not limited thereto. In some embodiments, steps S51 to S53 in FIG. 8 are repeatedly executed a designated preset number of times (predetermined times).

In the above embodiments, the case has been described in which the flare region removal processing is automatically preformed before starting the OCT measurement; however, the configuration of the ophthalmologic apparatus according to the embodiments is not limited thereto. In some embodiments, a first operation mode for automatically performing the flare region removal processing or a second operation mode for manually performing the flare region removal processing can be set in advance. In the first operation mode, the flare region removal processing is automatically performed before starting the OCT measurement as the above embodiments. In the second operation mode, the flare region removal processing is performed upon receiving an operation on the user interface 240.

In some embodiments, an operation button for switching between the first operation mode and the second operation mode is provided in the operation unit 240B. Thereby, it is possible to switch between the first operation mode and the second operation mode at the time of automatic photographing.

In some embodiments, an operation button for designating to perform the flare region removal processing is provided in the operation unit 240B. Thereby, the user can perform the flare region removal processing at a desired timing by operating on the operation button at the time of photographing manually.

In the above embodiments, the case has been described in which the movement mechanism 150 moves the optical system with respect to the subject's eye E to remove the flare region; however, the configuration of the ophthalmologic apparatus according to the embodiments is not limited thereto. In some embodiments, the movement mechanism 150 moves the member for supporting the face of the subject such as a chin rest.

In the above embodiments, the case has been described in which the fundus image of the subject's eye E is obtained using the imaging optical system 30; however, the configuration of the ophthalmologic apparatus according to the embodiments is not limited thereto. In some embodiments, the image of the fundus Ef is the front image of the fundus Ef formed based on the data acquired by OCT scan using the OCT unit 100. Examples of the front image of the fundus Ef include a C scan image, a shadowgram, a projection image, and the like. In the case that the ophthalmologic apparatus 1 includes a SLO optical system, the image of the fundus Ef may be a front image of the fundus obtained using the SLO optical system.

In some embodiments, the flare region removal processing in step S4 is executed after performing rough alignment in step S1 of FIG. 7.

<Actions and Effects>

Described below are the actions and effects of the ophthalmologic apparatus according to the embodiments.

An ophthalmologic apparatus (1) according to some embodiments includes a data acquisition unit (imaging optical system 30, optical system from the OCT unit 100 to the objective lens 22, or optical system included in the fundus camera unit 2), a movement mechanism (150), an image acquisition unit (imaging optical system 30 or optical system from the OCT unit 100 to the objective lens 22), an analyzer (231), and a controller (210, main controller 211). The data acquisition unit is configured to optically acquire data of a fundus (Ef) of a subject's eye (E). The movement mechanism is configured to change relative position between the subject's eye and the data acquisition unit. The image acquisition unit is configured to acquire an image of the fundus. The analyzer is configured to specify at least one of a relative movement direction and relative movement amount of the data acquisition unit with respect to the subject's eye based on a flare region in the image and a reference position in the image. The controller is configured to control the movement mechanism based on the at least one of the relative movement direction and the relative movement amount.

In such a configuration, at least one of the relative movement direction and the relative movement amount is specified based on the flare region in the image of the fundus of the subject's eye and the reference position in the image. And the relative position of the data acquisition unit with respect to the subject's eye is changed by controlling the movement mechanism. Thereby, the flare due to alignment error, displacement of optical elements, or the like can be removed with high accuracy and quickly in addition to when the subject's eye is directed obliquely due to the heterophoria or the like, when the cornea is distorted due to the disease of the cornea or the like, or when the subject's eye is a small pupil. It should be noted that a data processor may include the image acquisition unit.

In the ophthalmologic apparatus according to some embodiments, the analyzer is configured to specify a new relative movement direction based on the flare region and the reference position after relative movement by the movement mechanism and to specify new relative movement amount corresponding to a change in the flare region before and after the relative movement. The controller is configured to control the movement mechanism based on the new relative movement direction and the new relative movement amount, after controlling the movement mechanism so as to relatively move the data acquisition unit with respect to the subject's eye by predetermined amount in a relative movement direction specified before the relative movement.

According to such a configuration, the relative movement direction and the relative movement amount are specified based on the change in the flare region before and after the relative movement. Thereby, flare can be removed with absolute accuracy, irrespective of the state of the subject's eye or the state of the optical system of the apparatus.

In the ophthalmologic apparatus according to some embodiments, the analyzer is configured to specify the new relative movement amount so as to remove the flare region after the relative movement based on the change in the flare region.

According to such a configuration, flare can be removed quickly with absolute accuracy, irrespective of the state of the subject's eye or the state of the optical system of the apparatus.

In the ophthalmologic apparatus according to some embodiments, the analyzer is configured to specify the new relative movement amount so as not to increase the flare region in a direction opposite to the new relative movement direction.

According to such a configuration, flare can be removed while suppressing an increase in the flare region appeared in the direction opposite to the movement direction, by relatively moving.

The ophthalmologic apparatus according to some embodiments is configured to repeat a process of specifying the new relative movement direction and the new relative movement amount by the analyzer and a process of controlling the movement mechanism based on the new relative movement direction and the new relative movement amount by the controller a predetermined number of times.

According to such a configuration, a process of specifying the relative movement direction and the relative movement amount and a process of relatively moving are repeated a predetermined times. Thereby, flare can be removed quickly with absolute accuracy, irrespective of the state of the subject's eye or the state of the optical system of the apparatus.

The ophthalmologic apparatus according to some embodiments is configured to repeat a process of specifying the new relative movement direction and the new relative movement amount by the analyzer and a process of controlling the movement mechanism based on the new relative movement direction and the new relative movement amount by the controller until a size of the flare region becomes equal to or less than a predetermined value.

According to such a configuration, a process of specifying the relative movement direction and the relative movement amount and a process of relatively moving are repeated until the size of the flare region becomes equal to or less than the threshold value. Thereby, flare can be removed quickly with absolute accuracy, irrespective of the state of the subject's eye or the state of the optical system of the apparatus.

In the ophthalmologic apparatus according to some embodiments, the analyzer is configured to specify the at least one of the relative movement direction and the relative movement amount based on a radial length of the flare region centered on the reference position and the reference position.

According to such a configuration, the size of the flare region using the radial length of the flare region centered on the reference position of the image of the fundus is estimated. Thereby, the flare region can be removed with a simple process.

In the ophthalmologic apparatus according to some embodiments, the reference position is a center position of the image and the analyzer is configured to specify the relative movement direction based on a direction toward a representative position of the flare region from the center position.

According to such a configuration, the relative movement direction can be specified with a simple process.

In the ophthalmologic apparatus according to some embodiments, the representative position is a position of the center of gravity of the flare region.

According to such a configuration, the relative movement direction can be specified with a simple process.

In the ophthalmologic apparatus according to some embodiments, the data acquisition unit includes an optical system for acquiring the data of the fundus and the movement mechanism is configured to change the relative position between the subject's eye and the data acquisition unit in a direction crossing an optical axis of the optical system.

According to such a configuration, the flare region depicted at the edge part of the image of the fundus can be removed, irrespective of the state of the subject's eye or the state of the optical system of the apparatus.

In the ophthalmologic apparatus according to some embodiments, the controller is configured to control the movement mechanism based on the at least one of the relative movement direction and the relative movement amount, after performing alignment of the data acquisition unit with respect to the subject's eye based on a characteristic position of the subject's eye.

According to such a configuration, the flare region removal is performed after alignment is performed. Thereby, the flare region can be removed quickly and highly accurate data of the subject's eye can be acquired.

Some embodiments relate to a method of controlling an ophthalmologic apparatus (1). The ophthalmologic apparatus includes a data acquisition unit (imaging optical system 30, optical system from the OCT unit 100 to the objective lens 22, or optical system included in the fundus camera unit 2) configured to optically acquire data of a fundus (Ef) of a subject's eye (E), a movement mechanism (150) configured to change relative position between the subject's eye and the data acquisition unit, and a controller (210, main controller 211) configured to control the movement mechanism. The method of controlling the ophthalmologic apparatus includes an acquisition step, an analyzing step, and a control step. The acquisition step acquires the image of the fundus. The analyzing step specifies at least one of a relative movement direction and relative movement amount of the data acquisition unit with respect to the subject's eye based on a flare region in the image and a reference position in the image. The control step controls the movement mechanism based on the at least one of the relative movement direction and the relative movement amount.

In such a method, at least one of the relative movement direction and the relative movement amount is specified based on the flare region in the image of the fundus of the subject's eye and the reference position in the image. And the relative position of the data acquisition unit with respect to the subject's eye is changed by controlling the movement mechanism. Thereby, the flare due to alignment error, displacement of optical elements, or the like can be removed with high accuracy and quickly in addition to when the subject's eye is directed obliquely due to the heterophoria or the like, when the cornea is distorted due to the disease of the cornea or the like, or when the subject's eye is a small pupil.

In the method of controlling the ophthalmologic apparatus according to some embodiments, the analyzing step specifies a new relative movement direction based on the flare region and the reference position after relative movement by the movement mechanism and specifies new relative movement amount corresponding to a change in the flare region before and after the relative movement. The control step controls the movement mechanism based on the new relative movement direction and the new relative movement amount, after controlling the movement mechanism so as to relatively move the data acquisition unit with respect to the subject's eye by predetermined amount in a relative movement direction specified before the relative movement.

According to such a method, the relative movement direction and the relative movement amount are specified based on the change in the flare region before and after the relative movement. Thereby, flare can be removed with absolute accuracy, irrespective of the state of the subject's eye or the state of the optical system of the apparatus.

In the method of controlling the ophthalmologic apparatus according to some embodiments, the reference position is a center position of the image, and in the analyzing step, the relative movement direction is specified based on a direction toward a representative position of the flare region from the center position.

According to such a method, the relative movement direction can be specified with a simple process.

In the method of controlling the ophthalmologic apparatus according to some embodiments, the representative position is a position of the center of gravity of the flare region.

According to such a method, the relative movement direction can be specified with a simple process.

In the method of controlling the ophthalmologic apparatus according to some embodiments, the data acquisition unit includes an optical system for acquiring the data of the fundus, and the movement mechanism is configured to change the relative position between the subject's eye and the data acquisition unit in a direction crossing an optical axis of the optical system.

According to such a method, the flare region depicted at the edge part of the image of the fundus can be removed, irrespective of the state of the subject's eye or the state of the optical system of the apparatus.

The method of controlling the ophthalmologic apparatus according to some embodiments further includes a position matching step of performing alignment of the data acquisition unit with respect to the subject's eye based on a characteristic site of the subject's eye, wherein the control step is performed after the position matching step.

According to such a method, the flare region removal is performed after alignment is performed. Thereby, the flare region can be removed quickly and highly accurate data of the subject's eye can be acquired.

The embodiments described above are merely examples. One who intends to implement the present invention may arbitrarily modify (omission, replacement, addition, etc.) within the scope of the invention.

In some embodiments, a program for causing a computer to execute the method of controlling the ophthalmologic apparatus is stored in the storage unit 212. Such a program can be stored in any kind of recording medium that can be read by the computer. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
    a data acquisition unit configured to optically acquire data of a fundus of a subject's eye;
    a movement mechanism configured to change relative position between the subject's eye and the data acquisition unit;
    an image acquisition unit configured to acquire an image of the fundus;
    an analyzer configured to specify at least one of a relative movement direction and relative movement amount of the data acquisition unit with respect to the subject's eye based on a flare region in the image and a reference position in the image; and
a controller configured to control the movement mechanism based on the at least one of the relative movement direction and the relative movement amount, wherein
the analyzer is configured to specify a new relative movement direction based on the flare region and the reference position after relative movement by the movement mechanism, the analyzer is configured to specify a change in the flare region before and after the relative movement by the movement mechanism, and the analyzer is configured to specify a new relative movement amount corresponding to the specified change in the flare region,
the controller is configured to control the movement mechanism based on the new relative movement direction and the new relative movement amount, after controlling the movement mechanism so as to relatively move the data acquisition unit with respect to the subject's eye by a predetermined amount in a relative movement direction specified before the relative movement, and
the predetermined amount for relatively moving the data acquisition unit with respect to the subject's eye corresponds to an alignment error amount.

2. The ophthalmologic apparatus of claim 1, wherein the analyzer is configured to specify the new relative movement amount so as to remove the flare region after the relative movement based on the change in the flare region.

3. The ophthalmologic apparatus of claim 1, wherein the analyzer is configured to specify the new relative movement amount so as not to increase the flare region in a direction opposite to the new relative movement direction.

4. The ophthalmologic apparatus of claim 1, wherein a process of specifying the new relative movement direction and the new relative movement amount by the analyzer and a process of controlling the movement mechanism based on the new relative movement direction and the new relative movement amount by the controller are repeated a predetermined number of times.

5. The ophthalmologic apparatus of claim 1, wherein a process of specifying the new relative movement direction and the new relative movement amount by the analyzer and a process of controlling the movement mechanism based on the new relative movement direction and the new relative movement amount by the controller are repeated until a size of the flare region becomes equal to or less than a predetermined value.

6. The ophthalmologic apparatus of claim 1, wherein the analyzer is configured to specify the at least one of the relative movement direction and the relative movement amount based on a radial length of the flare region centered on the reference position and the reference position.

7. The ophthalmologic apparatus of claim 1, wherein the reference position is a center position of the image, and
the analyzer is configured to specify the relative movement direction based on a direction toward a representative position of the flare region from the center position.

8. The ophthalmologic apparatus of claim 7, wherein the representative position is a position of the center of gravity of the flare region.

9. The ophthalmologic apparatus of claim 1, wherein the data acquisition unit comprises an optical system for acquiring the data of the fundus, and
the movement mechanism is configured to change the relative position between the subject's eye and the data acquisition unit in a direction crossing an optical axis of the optical system.

10. The ophthalmologic apparatus of claim 1, wherein the controller is configured to control the movement mechanism based on the at least one of the relative movement direction and the relative movement amount, after performing alignment of the data acquisition unit with respect to the subject's eye based on a characteristic site of the subject's eye.

11. The ophthalmologic apparatus of claim 1, wherein the analyzer is further configured to specify the new relative movement amount corresponding to a change in a size of the flare region before and after the relative movement.

12. A method of controlling an ophthalmologic apparatus comprising a data acquisition unit configured to optically acquire data of a fundus of a subject's eye, a movement mechanism configured to change relative position between the subject's eye and the data acquisition unit, and a controller configured to control the movement mechanism, the method comprising:
an acquisition step of acquiring an image of the fundus;
an analyzing step of specifying at least one of a relative movement direction and relative movement amount of the data acquisition unit with respect to the subject's eye based on a flare region in the image and a reference position in the image; and
a control step of controlling the movement mechanism based on the at least one of the relative movement direction and the relative movement amount, wherein
in the analyzing step, a new relative movement direction is specified based on the flare region and the reference position after relative movement by the movement mechanism, a change in the flare region is specified before and after the relative movement by the movement mechanism, and a new relative movement amount corresponding to the specified change in the flare region is specified,
in the control step, the movement mechanism is controlled based on the new relative movement direction and the new relative movement amount, after controlling the movement mechanism so as to relatively move the data acquisition unit with respect to the subject's eye by predetermined amount in a relative movement direction specified before the relative movement, and
the predetermined amount for relatively moving the data acquisition unit with respect to the subject's eye corresponds to an alignment error amount.

13. The method of controlling the ophthalmologic apparatus of claim 12, wherein
the reference position is a center position of the image, and
in the analyzing step, the relative movement direction is specified based on a direction toward a representative position of the flare region from the center position.

14. The method of controlling the ophthalmologic apparatus of claim 13, wherein
the representative position is a position of the center of gravity of the flare region.

15. The method of controlling the ophthalmologic apparatus of claim 12, wherein
the data acquisition unit comprises an optical system for acquiring the data of the fundus, and
the movement mechanism is configured to change the relative position between the subject's eye and the data acquisition unit in a direction crossing an optical axis of the optical system.

16. The method of controlling the ophthalmologic apparatus of claim 12, further comprising:
a position matching step of performing alignment of the data acquisition unit with respect to the subject's eye based on a characteristic site of the subject's eye, wherein
the control step is performed after the position matching step.

17. An ophthalmologic apparatus comprising:
a first camera configured to optically acquire data of a fundus of a subject's eye;
an actuator configured to change relative position between the subject's eye and the data acquisition unit;
a second camera configured to acquire an image of the fundus;
an analyzer circuit configured to specify at least one of a relative movement direction and relative movement amount of the data acquisition unit with respect to the subject's eye based on a flare region in the image and a reference position in the image; and
a controller circuit configured to control the actuator based on the at least one of the relative movement direction and the relative movement amount, wherein
the analyzer circuit is configured to specify a new relative movement direction based on the flare region and the reference position after relative movement by the actuator and, the analyzer circuit is configured to specify a change in the flare region before and after the relative movement by the movement mechanism, and the analyzer circuit is configured to specify a new relative movement amount corresponding to the specified change in the flare region,
the controller circuit is configured to control the actuator based on the new relative movement direction and the new relative movement amount, after controlling the actuator so as to relatively move the first camera with respect to the subject's eye by a predetermined amount in a relative movement direction specified before the relative movement, and
the predetermined amount for relatively moving the first camera with respect to the subject's eye corresponds to an alignment error amount.

* * * * *